US011986033B2

(12) United States Patent
Ben-Tzvi et al.

(10) Patent No.: US 11,986,033 B2
(45) Date of Patent: May 21, 2024

(54) ROBOTIC EXOSKELETON GLOVE SYSTEM

(71) Applicant: VIRGINIA TECH INTELLECTUAL PROPERTIES, INC., Blacksburg, VA (US)

(72) Inventors: Pinhas Ben-Tzvi, Blacksburg, VA (US); Bijo Sebastian, Blacksburg, VA (US); Eric M. Refour, Blacksburg, VA (US); Wenda Xu, Blacksburg, VA (US); Sarthak Pradhan, Blacksburg, VA (US); Yunfei Guo, Blacksburg, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 474 days.

(21) Appl. No.: 16/888,993

(22) Filed: Jun. 1, 2020

(65) Prior Publication Data
US 2020/0375287 A1 Dec. 3, 2020

Related U.S. Application Data

(60) Provisional application No. 62/855,967, filed on Jun. 1, 2019.

(51) Int. Cl.
*A61F 5/01* (2006.01)
*A41D 19/00* (2006.01)
(Continued)

(52) U.S. Cl.
CPC .......... *A41D 19/0027* (2013.01); *A61F 2/586* (2013.01); *A61F 4/00* (2013.01);
(Continued)

(58) Field of Classification Search
None
See application file for complete search history.

(56) References Cited

U.S. PATENT DOCUMENTS 10,011,019 B1 * 7/2018 Strauss ................. B25J 15/022

FOREIGN PATENT DOCUMENTS

CN 106214425 A * 12/2016 ........... A61H 1/0288
CN 108814898 A * 11/2018 ........... A61H 1/0288
(Continued)

OTHER PUBLICATIONS

Espacenet translation of CN 109199784 A, published on Jan. 15, 2019.*
(Continued)

*Primary Examiner* — David H Willse
(74) *Attorney, Agent, or Firm* — Perilla Knox & Hildebrandt LLP; Jason M. Perilla

(57) ABSTRACT

An assistive exoskeleton glove system for a hand of an individual is described. In one example, the system includes a brace mount and a finger brace including a seat platform mechanically coupled to the brace mount. The finger brace can include a plurality of brace links, a plurality of constraint links, and an actuation lever. The system can also include an actuator mechanically coupled to the actuation lever and configured to articulate the finger brace over a predetermined range of motion. The range of motion can be tailored for different purposes. The system can also include finger abduction and adduction mechanisms, a thumb brace, a thumb flexion actuator, and a control system. The control system can be configured to detect a relative difference in feedback signals provided from target and offset encoders on the finger brace, as an input to control the actuator, and real-time grasping forces among other inputs.

16 Claims, 9 Drawing Sheets

(51) Int. Cl.

| | | |
|---|---|---|
| *A61F 2/58* | (2006.01) | |
| *A61F 4/00* | (2006.01) | |
| *A61H 1/02* | (2006.01) | |
| *G06F 3/01* | (2006.01) | |
| *A61F 2/76* | (2006.01) | |

(52) U.S. Cl.
CPC .......... *A61F 5/0118* (2013.01); *A61F 5/013* (2013.01); *A61H 1/0288* (2013.01); *G06F 3/014* (2013.01); *G06F 3/016* (2013.01); *A61F 2002/587* (2013.01); *A61F 2002/7625* (2013.01); *A61F 2002/7635* (2013.01); *A61F 2005/0141* (2013.01); *A61F 2005/0144* (2013.01); *A61F 2005/0151* (2013.01); *A61F 2005/0155* (2013.01); *A61F 2005/0179* (2013.01); *A61F 2005/0188* (2013.01); *A61H 2205/067* (2013.01)

(56) References Cited

FOREIGN PATENT DOCUMENTS

| CN | 109199784 A | * | 1/2019 | ........... A61H 1/0285 |
| CN | 109646156 A | * | 4/2019 | ............... A61H 1/02 |
| EP | 0 280 324 A1 | * | 8/1988 | ............... B25J 9/18 |
| RU | 169 865 U1 | * | 4/2017 | |

OTHER PUBLICATIONS

Z. Ma and P. Ben-Tzvi, "An Admittance-Type Haptic Device—RML Glove," ASME Int. Mech. Eng. Congr. Expo., pp. 1-7, 2011.

Pratt, J., Krupp, B., Morse, C., Pratt, J., and Krupp, B., 2002, "Feature Series Elastic Actuators for High Fidelity Force Control," Ind. Rob: Int. J., 29(3), pp. 234-241.

Refour, E., Sebastian, B., Ben-Tzvi, P., "Two-Digit Robotic Exoskeleton Glove Mechanism: Design and Integration", Journal of Mechanisms and Robotics, Transactions of the ASME, vol. 10, Issue 2, pp. 025002: 1-9, Apr. 2018.

Bekey, G. A., Tomovic, R., and Zeljkovic, I., 1990, "Control Architecture for the Belgrade/USC Hand," Dexterous Robot Hands, S. T. Venkataraman and T. Iberall, eds., Springer, New York, pp. 136-149.

Liu, M., and Xiong, C., 2014, "Synergistic Characteristic of Human Hand During Grasping Tasks in Daily Life," International Conference on Intelligent Robotics and Applications (ICIRA), Guangzhou, China, Dec. 17-20, pp. 67-76.

M.-J. Liu, C.-H. Xiong, L. Xiong, and X.-L. Huang, "HUST dataset," Jan. 5, 2016. [Online]. Available: http://www.handcorpus.org/?p=1596.

Chauhan, R. J., and Ben-Tzvi, P., 2018, "Latent Variable Grasp Prediction for Exoskeletal Glove Control," Proceedings of ASME Dynamic Systems and Control, Atlanta, GA, Sep. 30-Oct. 3.

Vanteddu, T., Sebastian, B., and Ben-Tzvi, P., 2018. "Design Optimization of RML Glove for Improved Grasp Performance". In Proceedings of the ASME 2018 Dynamic Systems and Control Conf. (DSCC 2018), pp. 1-8.

M. Ebden, "Gaussian processes: A quick introduction," Aug. 2015. [Online]. Available: https://arxiv.org/pdf/1505.02965.pdf.

Lee, B. J., Williams, A., and Ben-Tzvi, P., 2018, "Intelligent Object Grasping With Sensor Fusion for Rehabilitation and Assistive Applications," IEEE T. Neur. Syst. Rehabil. Eng., 26(8), pp. 1556-1565.

Hara, A., Yamauchi, Y., and Kusunose, K., 1994, "Analysis of Thumb and Index Finger Joints During Pinching Motion and Writing a Cross, as Measured by Electrogoniometers," Clinical Biomechanics and Related Research, Y. Hirasawa, C. B. Sledge, and S. L.-Y. Woo, eds., Springer, Tokyo, Japan, pp. 282-293.

Pratt, G. A., and Williamson, M. M., 1995, "Series Elastic Actuators," IEEE/RSJ International Conference on Intelligent Robots and Systems, Pittsburgh, PA, Aug. 5-9, pp. 399-406.

Mathiowetz, V., Kashman, N., Volland, G., Weber, K., Dowe, M., and Rogers, S., 1985, "Grip and Pinch Strength: Normative Data for Adults," Arch. Phys. Med. Rehab., 66(2), pp. 69-74.

Feix, T., Romero, J., Schmiedmayer, H. B., Dollar, A. M., and Kragic, D., 2016, "The GRASP Taxonomy of Human Grasp Types," IEEE T. Hum-Mach. Syst., 46(1), pp. 66-77.

* cited by examiner

ROBOTIC EXOSKELETON GLOVE SYSTEM

CROSS-REFERENCE TO RELATED APPLICATIONS

This application claims the benefit of U.S. Provisional Application No. 62/855,967, filed Jun. 1, 2019, the entire contents of which is hereby incorporated herein by reference.

STATEMENT REGARDING FEDERALLY SPONSORED RESEARCH OR DEVELOPMENT

This invention was made with government support under grant number R21HD095027, awarded by the National Institutes of Health. The government has certain rights in the invention.

BACKGROUND

Over the past few decades, exoskeleton and haptic gloves have emerged in popularity in the fields of virtual reality (VR) and medical applications, among others. In the realm of VR, for example, exoskeleton and haptic gloves have been used to create realistic experiences by generating tactile responses to reflect the sensation of the user touching an object. Within the medical field, exoskeleton gloves are used in numerous ways, including as an assistive tool for tele-operated surgeries and as a rehabilitation tool for people who suffer from paralysis in the hand and/or fingers. Unfortunately, many commercially-available exoskeleton and haptic gloves are expensive and require complex equipment, making them unwieldy and less portable for activities of daily living.

BRIEF DESCRIPTION OF THE DRAWINGS

Aspects of the present disclosure can be better understood with reference to the following drawings. It is noted that the elements in the drawings are not necessarily to scale, with emphasis instead being placed upon clearly illustrating the principles of the embodiments. In the drawings, like reference numerals designate like or corresponding, but not necessarily the same, elements throughout the several views.

DETAILED DESCRIPTION

Figure 1:
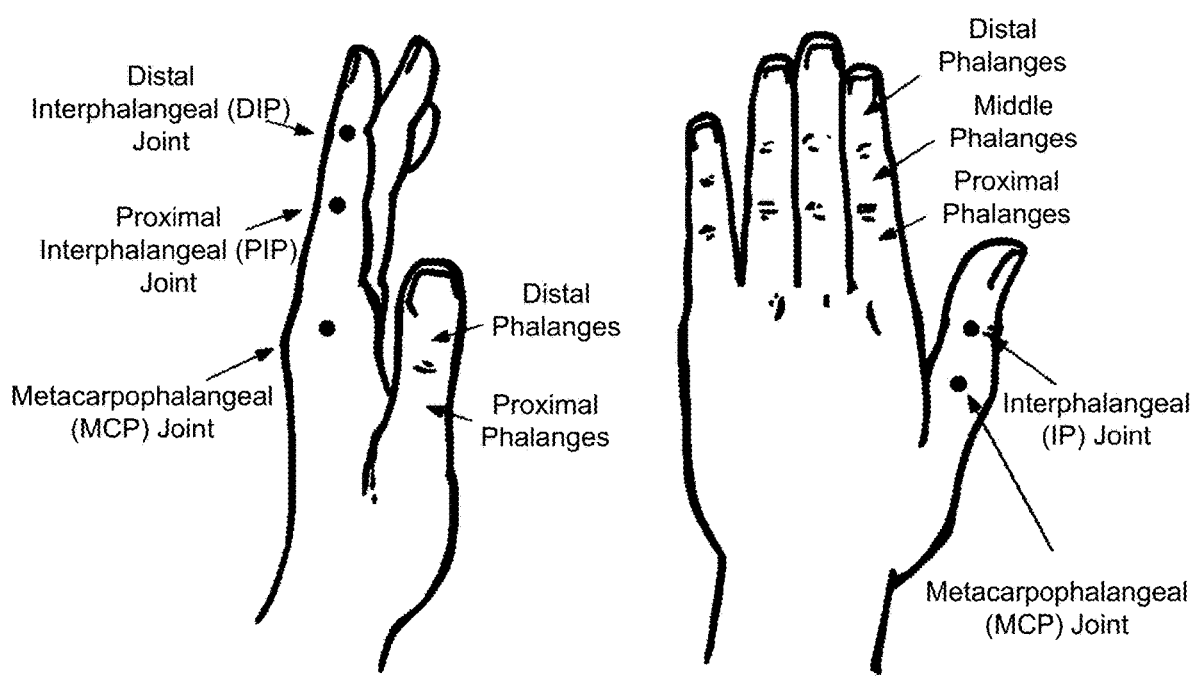
FIG. 1 illustrates an example of the major joints on a human hand for discussion.

As noted above, robotic exoskeleton and haptic gloves have emerged in popularity in the fields of virtual reality (VR) and medical applications, among others. In the realm of VR, for example, exoskeleton and haptic gloves have been used to create realistic experiences by generating tactile responses to reflect the sensation of the user touching an object. Within the medical field, exoskeleton gloves are used in numerous ways, including as an assistive tool for tele-operated surgeries and as a rehabilitation tool for people who suffer from paralysis in the hand and/or fingers. Unfortunately, many commercially-available exoskeleton and haptic gloves are expensive and require complex equipment, making them unwieldy and less portable for activities of daily living.

There have been two main approaches, rigid and soft designs, for exoskeleton gloves over the years. One traditional approach involves the use of rigid links and joints to apply forces to the corresponding joints of the hand, providing flexion and extension. Rigid gloves have better force transmission than soft gloves and can achieve grasp configurations more easily. Most of these exoskeleton gloves are designed with the link frames placed on top of the fingers and hand, rather than alongside the fingers. This is primarily due to the fact that the size of the link frames exceeds the available space between fingers. The currently-available rigid exoskeleton gloves have a number of disadvantages. For example, conventional exoskeleton gloves are often heavy, bulky, not portable, and can hinder the natural motion of the hand.

Soft gloves are often actuated using cables in various ways, including routing through thermoplastic guides, anchoring about thimble-like straps, and using soft tendon routing mechanisms and related cable systems to keep the actuation system at a remote location. Special inflatable polymers, which can bend to produce desired grasping motions, have also been used to build soft gloves. There are several materials and types of actuation methods, such as using pneumatics, air muscles integrated with linkages, and molded elastomeric chambers that bend using fluid pressure, among others. These approaches focus on using tendon-driven design, or elastic polymers as inflatable membranes which expand to achieve desired bending profiles.

Unfortunately, soft designs have significant disadvantages. As examples, soft gloves can produce discomfort due to the pre-tensioning of cables, experience loss in efficiency caused by friction along the cable paths, and exhibit the creation of shear forces applied onto soft backing materials during flexion and extension. These factors, among others, hinder the effective force transmission in soft tendon or cable driven systems. Soft inflatable gloves, on the other hand, are generally unable to provide natural flexion and extension profiles for the human finger and are therefore limited to the basic configurations of fully-open or fully-closed fists in many cases.

To be effective as an assistive and rehabilitation device for activities of daily living, an assistive glove should be able to interact with objects over a wide range of sizes. For example, the assistive system should be able to grasp various types and sizes of objects. Experimental validation results have shown that the existing designs of many exoskeleton gloves cannot produce finger trajectories suitable for grasping many cylindrical objects, such as those with a diameter of less than 100 mm.

In order to address the challenges and drawbacks of conventional designs, a new assistive exoskeleton glove system is described herein. One distinguishing factor of the system is the use of linkage mechanisms slim enough to fit between the fingers, resulting in a lightweight, low profile system. In addition, each finger of the exoskeleton glove system is designed to be actuated as a single degree of freedom (DoF) mechanism. Each finger can be actuated using a single motor or actuator while following a trajectory modelled after a healthy human hand.

In one aspect of the embodiments, the kinematics of the flexion brace linkage mechanisms for fingers and thumbs, as described herein, were analyzed in detail, and the design variables were identified. Different cost functions were formulated and compared in their ability to yield optimal values for the design variables. An optimal set of design variables was chosen in one example, based on the grasp angles achieved. The resulting mechanism was simulated for feasibility and testing. An exoskeleton mechanism corresponding to the index finger was manufactured with the chosen design variables and experimental validation was performed to illustrate the improvement in grasp performance over existing designs. Thus, in one aspect of the embodiments, the exoskeleton glove systems described herein can be optimized to enable grasping smaller diameter objects. In another aspect of the embodiments, the exoskeleton glove systems described herein can be optimized to enable grasping larger diameter objects.

Among other advantages, the embodiments presented herein are designed to overcome the previously-mentioned drawbacks of traditional hard and soft exoskeleton gloves. The exoskeleton glove systems are intended to be general purpose, possessing the ability to serve as a medical device, virtual reality haptic glove, or for other purposes. The glove systems described herein are designed to assist individuals with grasping motions, such as the pincer grasp, the palm grasp, and other grasp forms, while maintaining a natural coupling relationship among the finger and thumb joints, resembling that of a normal human hand.

The designs can be actuated using a single DoF linkage mechanism to achieve active flexion and extension of the fingers and thumb. This greatly reduces the overall weight and size of the system, making it more suitable for prolonged usage. The mechanical and electromechanical designs, modeling, and control system architectures of the glove systems are described herein. In one example, the glove system is capable of recording absolute and relative position and/or orientation information about the positions of the fingers and thumb. The glove system can also track, monitor, and record the movements and interaction forces on the fingers and thumb and provide feedback through vibration. In addition, the glove system can serve as a standalone device for rehabilitation purposes, such as assisting in various types of grasping and pinching motions.

Turning to the drawings, FIG. 1 illustrates an example of the major joints on a human hand for discussion. As shown, each finger consists of three main joints, including the metacarpophalangeal (MCP), proximal interphalangeal (PIP), and distal interphalangeal (DIP) joints. The thumb includes the interphalangeal (IP) and MCP joints. To design an exoskeleton glove that satisfies the goals described herein, existing studies on human grasping motions, such as the common pinch, were considered. Experiments were performed to measure the joint angles for the index finger and thumb during a tip-pinch motion. The data was used as a reference to design features of the exoskeleton gloves described herein.

One conclusion drawn from the experiments is the existence of inherent coupling among the MCP, PIP and DIP joints of the human finger and the IP and MCP joints of the human thumb. As a result of this coupling, the human fingers and thumb each behave in large part as a single DoF system when flexing and extending to perform common grasping motions. This factor is relied upon by the designs described herein to reduce the number of actuators needed, which reduces the overall size and weight of the system.

Figure 2:
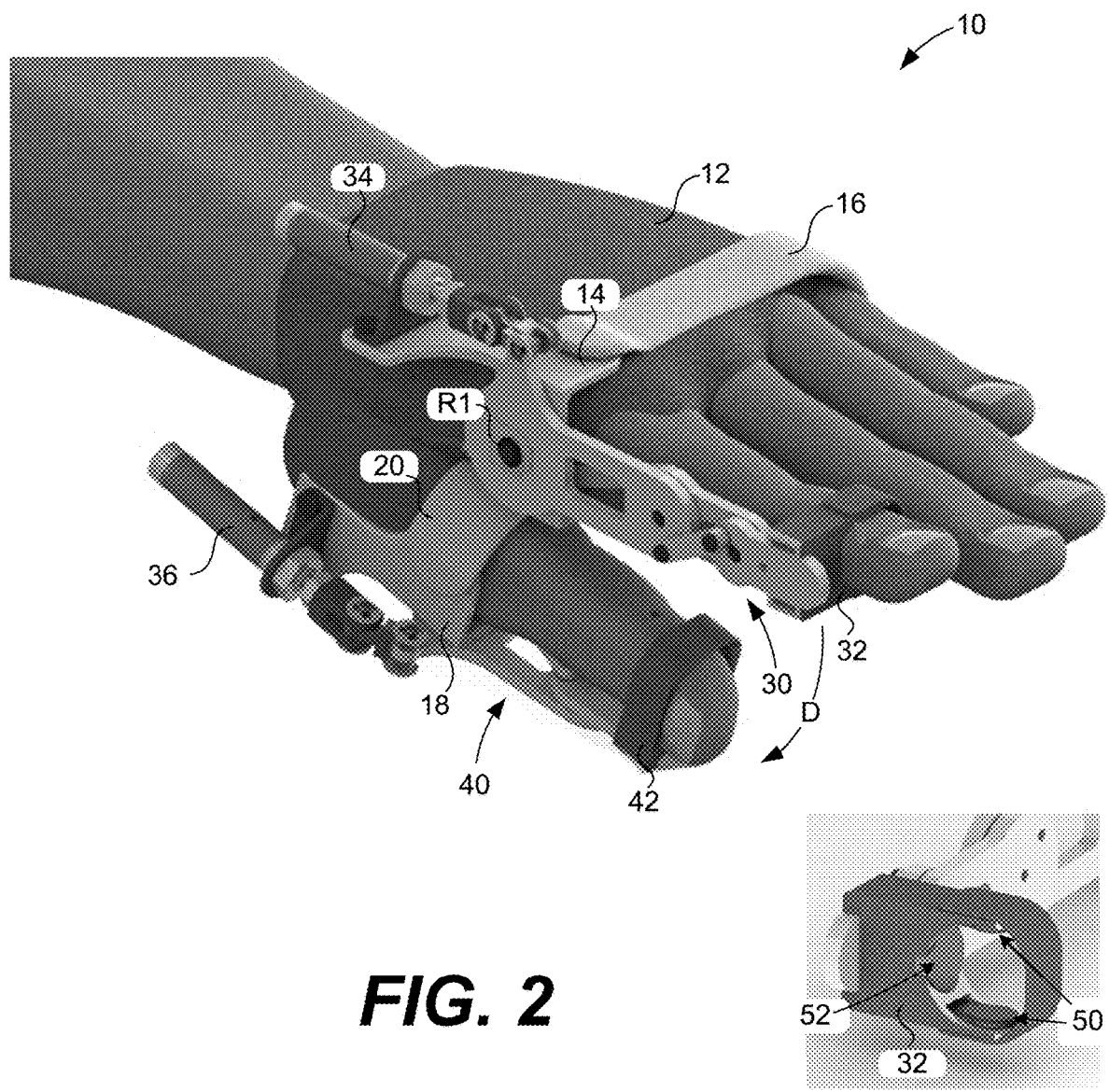
FIG. 2 illustrates an example exoskeleton glove system according to various aspects of the embodiments of the present disclosure.

FIG. 2 illustrates an example assistive exoskeleton glove system 10 ("glove system 10") according to various aspects of the embodiments of the present disclosure. The glove system 10 is provided as a representative example to introduce the concepts described herein. The glove system 10 is not necessarily drawn to scale in FIG. 2, nor does FIG. 2 provide an exhaustive illustration of all components of the glove system 10. Additionally, one or more of the components shown in FIG. 2 can be omitted in some cases. Variations on the glove system 10 are described in further detail below.

Among other components, the glove system 10 includes a glove 12, a palm brace platform 14, a palm brace strap 16, a thumb brace 18, a thumb brace strap 20, a finger flexion brace 30, a finger harness 32, a finger actuator 34, a thumb flexion brace 40, a thumb harness 42, and a thumb actuator 36. The glove 12 can be embodied as any covering for the palm of the human hand and may be formed from any suitable material(s). As examples, the glove 12 can be formed as a knit or woven material, from leather, from plastic or rubber, or other materials. The glove 12 fits over the palm of the hand, protects the palm, and provides a foundation for other components of the glove system 10 to be secured to the palm.

The palm brace platform 14 is designed to fit around the MCP joint of the index finger of the hand. The palm brace strap 16 is connected at one end to the palm brace platform 14, wraps around the palm (near the MCP joints in the hand), and can be secured at another end to the palm brace platform 14 as shown in FIG. 2. The palm brace platform 14, when secured to the hand with the palm brace strap 16, provides a relatively stable platform for the finger flexion brace 30. The finger flexion brace 30 is secured to the palm brace platform 14 at the revolute joint R1 and pivots with respect to the palm brace platform 14 at the revolute joint R1. The palm brace platform 14 can be formed from one or more suitable materials, including plastic(s), metal(s), wood, rubber(s), combinations thereof, or other materials. The palm brace strap 16 can be formed from fabric(s), plastic(s), metal(s), rubber(s), combinations thereof, or other suitable materials.

The thumb brace 18 is designed to fit around the MCP joint and/or thenar region of the thumb of the hand. The thumb brace strap 20 is connected at one end to the thumb brace 18, wraps around the MCP joint and/or thenar region, and can be secured at another end to the thumb brace 18 as shown in FIG. 2. The thumb brace 18 provides a relatively stable platform for the thumb flexion brace 40. The thumb flexion brace 40 is secured to the thumb brace 18 at a revolute joint (not shown) and pivots with respect to the thumb brace 18 at the revolute joint. The thumb brace 18 can be formed from one or more suitable materials, including plastic(s), metal(s), wood, rubber(s), combinations thereof, or other materials. The thumb brace strap 20 can be formed from fabric(s), plastic(s), metal(s), rubber(s), combinations thereof, or other suitable materials.

The finger actuator 34 is secured to the palm brace platform 14. A shaft of the finger actuator 34 is coupled at one end to an actuation lever of the finger flexion brace 30, as shown in FIG. 2. When actuated, the finger actuator 34 can extend or retract the shaft to articulate and curl the finger flexion brace 30 in the direction D. The mechanical arrangement and articulation of the finger flexion brace 30 is described in greater detail below. The finger actuator 34 is illustrated as an example of a linear actuator in FIG. 2. In various embodiments, the finger actuator 34 can be embodied as a hydraulic, pneumatic, piezoelectric, electromechanical, or other type of linear actuator. In some examples, the finger actuator 34 can include one or more elastic elements, to act as a series elastic actuator. Other features of linear actuators according to the embodiments are described in further detail below.

The thumb actuator 36 is secured to the thumb brace 18. A shaft of the thumb actuator 36 is coupled at one end to a lever of the thumb flexion brace 40. When actuated, the thumb actuator 36 can extend or retract the shaft to articulate and bend the thumb flexion brace 40. The mechanical arrangement and articulation of the thumb flexion brace 40 is described in greater detail below. The thumb actuator 36 can be embodied as a hydraulic, pneumatic, piezoelectric, electromechanical, or other type of linear actuator. In some examples, the thumb actuator 36 can include one or more elastic elements, to act as a series elastic actuator.

The finger flexion brace 30 is designed as a single DoF system. Particularly, the finger flexion brace 30 is designed to articulate with a curling or grasping motion based on a single, linear motion provided by the finger actuator 34. One key characteristic of the finger flexion brace 30 is its relatively thin profile. Flexion braces of a similar design can be positioned between one or more of the index finger and the middle finger, the middle finger and the ring finger, the ring finger and the pinky finger, and outside the pinky finger of the hand. Thus, the finger flexion brace 30 of the glove system 10 can be extended for use with other digits other than the index finger and thumb, as outlined in the examples below. The glove system 10 can also include a separate actuator for each additional flexion brace. Although not shown in FIG. 2, the glove system 10 can also include a control and feedback system, and those features are described in more detail below.

For absolute and/or relative position sensing, an encoder can be placed on the $R_1$ joint of the finger flexion brace 30, among other suitable joints. An encoder can also be placed at a similar location on a joint of the thumb flexion brace 40. Signals from the encoders can be captured by a control system, as described in greater detail below, and correspond to the angular position of the $L_1$ links of the braces 30 and 40. The encoders can be calibrated with the control system for accuracy. The remaining joint angles of the PIP and DIP joints of the index finger and the IP joint of the thumb can be calculated by the control system using the kinematic models of the braces 30 and 40. Using the kinematic model, the position of the final link corresponding to the distal phalanges of the finger and thumb, can also be calculated.

Referring again to FIG. 2, force sensors 50, such as force sensitive resistors (FSR) or other suitable sensors, can be used to measure the amount of force being applied to the index finger at the finger harness 32, during grasping. Two force sensors 50 can be positioned in the finger harness 32 at the end of each finger as shown in FIG. 2. In addition to the force sensors 50, a haptic feedback device 52 can also be incorporated into the finger harness 32, to provide feedback to the user. This feedback can be used in several applications, such as providing haptic feedback for virtual reality applications, acting as a stimulus to prompt the user to perform certain tasks for rehabilitation, or as feedback for tele-navigation.

Figure 3A:
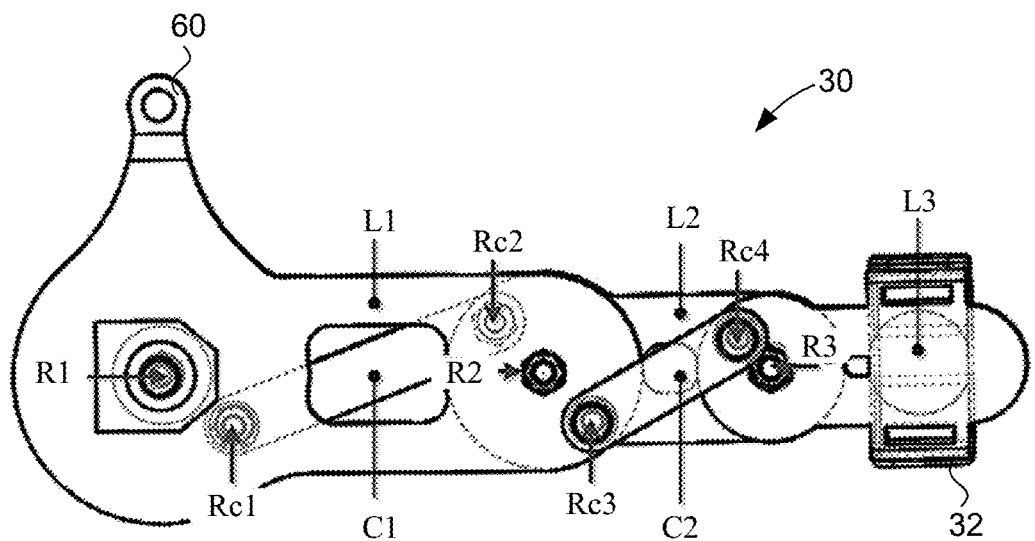
FIG. 3A illustrates an example flexion brace of the exoskeleton glove system shown in FIG. 2 according to various aspects of the embodiments of the present disclosure.

FIG. 3A illustrates the finger flexion brace 30 of the glove system 10 shown in FIG. 2. The finger flexion brace 30 includes links L1, L2, and L3, which correspond to the proximal, middle, and distal phalanges of the finger, respectively. The finger flexion brace 30 also includes constraint links C1 and C2. The links L1, L2, and L3 are connected to each other through three revolute joints, R1, R2, and R3. Specifically, links Li and Li+1 are connected through revolute joint Ri+1. The constraint links C1 and C2 are used to produce the coupling relationship between the Li links. The constraint link C1 connects the link L2 to a fixed base frame (ground) by revolute joints Rc1 and Rc2. The constraint link C2 connects links L1 and L3 through revolute joints Rc3 and Rc4. In the mechanical arrangement of the finger flexion brace 30, link L1 is connected to the ground at joint R1, link L1 is connected to link L2 at joint R2, and link L2 is connected to link L3 at joint R3. Additionally, constraint link C1 connects to the ground at constraint joint Rc1 and to link L2 at constraint joint Rc2, and constraint link C2 connects to link L1 at constraint joint Rc3 and to link L3 at constraint joint Rc4.

Figure 3B:
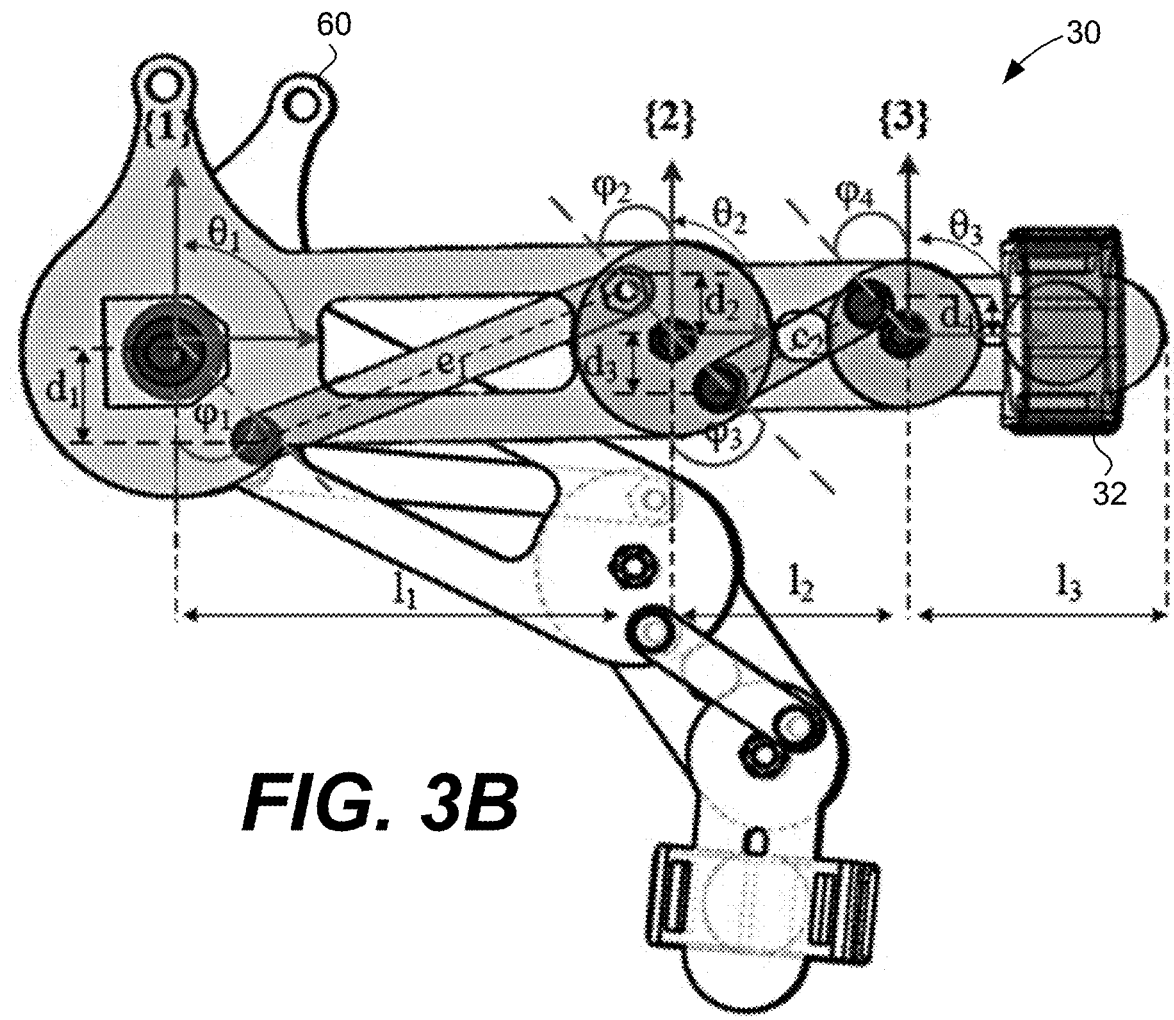
FIG. 3B illustrates flexion and extension motions of the flexion brace shown in FIG. 3A according to various aspects of the embodiments of the present disclosure.

FIG. 3B illustrates flexion and extension motions of the finger flexion brace 30. The flexion and extension motions can be achieved when a rotary motion is applied about the joint $R_1$, by pushing and pulling on the actuation lever 60 of link $L_1$. This motion causes link $L_1$ to rotate about the joint $R_1$. As the link $L_1$ bends, the constraint links $C_1$ and $C_2$ translate the motion along to links $L_2$ and $L_3$, as illustrated in FIG. 3B. This collectively provides the coupling motion that reflects the natural flexion and extension of a human finger.

To design the finger flexion brace 30, the lengths of the links, lengths of the constraint links, and positions of the revolute joints were determined based on the general dimensions of a human hand and the joint angles desired to be achieved. A kinematic model was relied upon for this purpose. The kinematic model accounted for the following design parameters, as identified in FIG. 3B: $l_i$—length of link $L_i$, $c_i$—length of constraint link $C_i$, $\theta_i$—joint angle of link $L_i$, $d_i$—the radial distance of constraint joint $Rc_i$, expressed in local coordinates, and $\varphi_i$—the angle made by constraint joint $Rc_i$ in respect to the vertical Y axis. For the design and simulations described herein, suitable dimensions for the lengths of the links, lengths of the constraint links, and positions of the revolute joints were selected based on typical dimensions of a human hand, but other dimensions can be used in various embodiments.

The degrees of freedom of the finger flexion brace 30 can be expressed in the coordinates corresponding to the following three planar links: [$(x_1, y_1, \theta_1)$, $(x_2, y_2, \theta_2)$, and $(x_3, y_3, \theta_3)$]. Establishing $\theta_1$ as the input variable in modeling for the finger flexion brace 30 yields the following eight constraint equations:

$$x_1 = 0, \tag{1}$$

$$y_1 = 0, \tag{2}$$

$$x_2 = x_1 + l_1 \cos \theta_1, \tag{3}$$

$$y_2 = y_1 + l_1 \sin \theta_1, \tag{4}$$

$$x_3 = x_2 + l_2 \cos \theta_2, \tag{5}$$

$$y_3 = y_2 + l_2 \sin \theta_2, \tag{6}$$

$$c_1^2 = [x_2 + (-d_2 \sin \varphi_2 \cos \theta_2) - d_2 \cos \varphi_2 \sin \theta_2 - d_1 \sin \varphi_1]^2 + [y_2 + (-d_2 \sin \varphi_2 \sin \theta_2) + d_2 \cos \varphi_2 \cos \theta_2 - d_1 \cos \varphi_1]^2, \text{ and} \tag{7}$$

$$c_2^2 = [x_1 + (l_1 + d_3 \sin \varphi_3 \cos \theta_1) - (-d_3 \cos \varphi_3 \sin \theta_1) - x_3 - (-d_4 \sin \varphi_4 \cos \theta_3) + d_4 \cos \varphi_4 \sin \theta_3]^2 + [y_1 + (l_1 + d_3 \sin \varphi_3 \sin \theta_1) - (-d_3 \cos \varphi_3 \cos \theta_1) - y_3 - (-d_4 \sin \varphi_4 \sin \theta_3) + d_4 \cos \varphi_4 \cos \theta_3]^2 \tag{8}$$

For equations (1)-(8), the constraint links $C_i$ are considered to be absolute distance constraints. For the kinematic model, the link lengths $L_i$ were set to general dimensions of a human hand. The other design parameters were estimated using a MATLAB® simulation, so that the joint angles achieved by the mechanism matched with the joint angles of a finger. The results confirm that the finger flexion brace 30 is capable of enforcing joint angles resembling that of a natural human hand.

The mechanical arrangement of the thumb flexion brace 40 is similar to the finger flexion brace 30, but the thumb flexion brace 40 includes only links $L_1$ and $L_2$, which are connected by revolute joint $R_2$. Thus, the design procedure for the thumb flexion brace 40 follows the same steps as described above for the finger flexion brace 30, but with only two main links $L_i$ and one constraint link $C_i$. The coupling action for the thumb flexion brace 40 is achieved by a constraint link $C_1$, which connects link $L_2$ to the base frame through revolute joints $Rc_1$ and $Rc_2$. The degrees of freedom of the thumb flexion brace 40 can be expressed in the coordinates corresponding to the following planar links: [$(x_1, y_1, \theta_1)$ and $(x_2, y_2, \theta_2)$]. In one example, the thumb flexion brace 40 offers MCP and IP angles of 19° and 17°, respectively. The results of modeling also confirm that the thumb flexion brace 40 mechanism is capable of exhibiting joint angles resembling that of a natural human hand.

One or more design variables of the finger flexion brace 30 can be optimized based on the kinematic model described above, among other relevant models. Similarly, one or more design variables of the thumb flexion brace 40 can be optimized based on relevant kinematic models. Further, flexion braces for the middle, ring, and pinky fingers can also be optimized for a number of design variables, if relied upon in the glove system 10.

All optimizations are constrained by the typical size of human fingers, which ranges for the thumb, index finger, middle finger, ring finger, and pinky finger. Thus, to start an optimization for a certain objective, the dimensions of the links L1, L2, and L3 can be selected to provide a comfortable fit for an averaged size adult. With those parameters fixed, an optimization can be performed on the other design variables, including $d_1$, $d_2$, $d_3$, $d_4$, $\varphi_1$, $\varphi_2$, $\varphi_3$ and $\varphi_4$ for larger or smaller values of $\theta_2$ and $\theta_3$, among other variables.

The optimization process can involve an objective or cost function, design variables, and the linear and non-linear constraints to be followed during the optimization. The optimization process can find the values for the design variables that maximize the objective function while satisfying the constraints. One example optimization function is a weighted sum of squared error of the joint angles θ1, θ2 and θ3 between the kinematic model and biomechanical data on the typical trajectory of a human grasp. This approach might produce design metrics that satisfy the points on the trajectory for an average grasp, for example, although other optimization functions can be used. As another example, the approach might seek to produce a trajectory to grasp relatively smaller objects or relatively larger objects. To be useful as an assistive device, the tip force may also be optimized to ensure it falls within an acceptable range for grasping objects. The tip force determines the maximum weight of the object that can be grasped without slippage, to ensure safe handling. In order to determine the tip force, the analytical relations between the input force from the actuator and the output tip force can be relied upon.

A number of example optimizations are described in the publication titled "Design Optimization of RML Glove for Improved Grasp Performance," proceedings of the ASME 2018 Dynamic Systems and Control Conference, Volume 1, Paper No. DSCC2018-9004 V001T07A004, published Nov. 12, 2018, the entire contents of which is hereby incorporated herein by reference. A number of other example optimizations are described in the publication titled "A General Purpose Robotic Hand Exoskeleton With Series Elastic Actuation," ASME Journal of Mechanisms and Robotics, Paper No. JMR-19-1086, published Sep. 10, 2019, the entire contents of which is hereby incorporated herein by reference.

Figure 4:
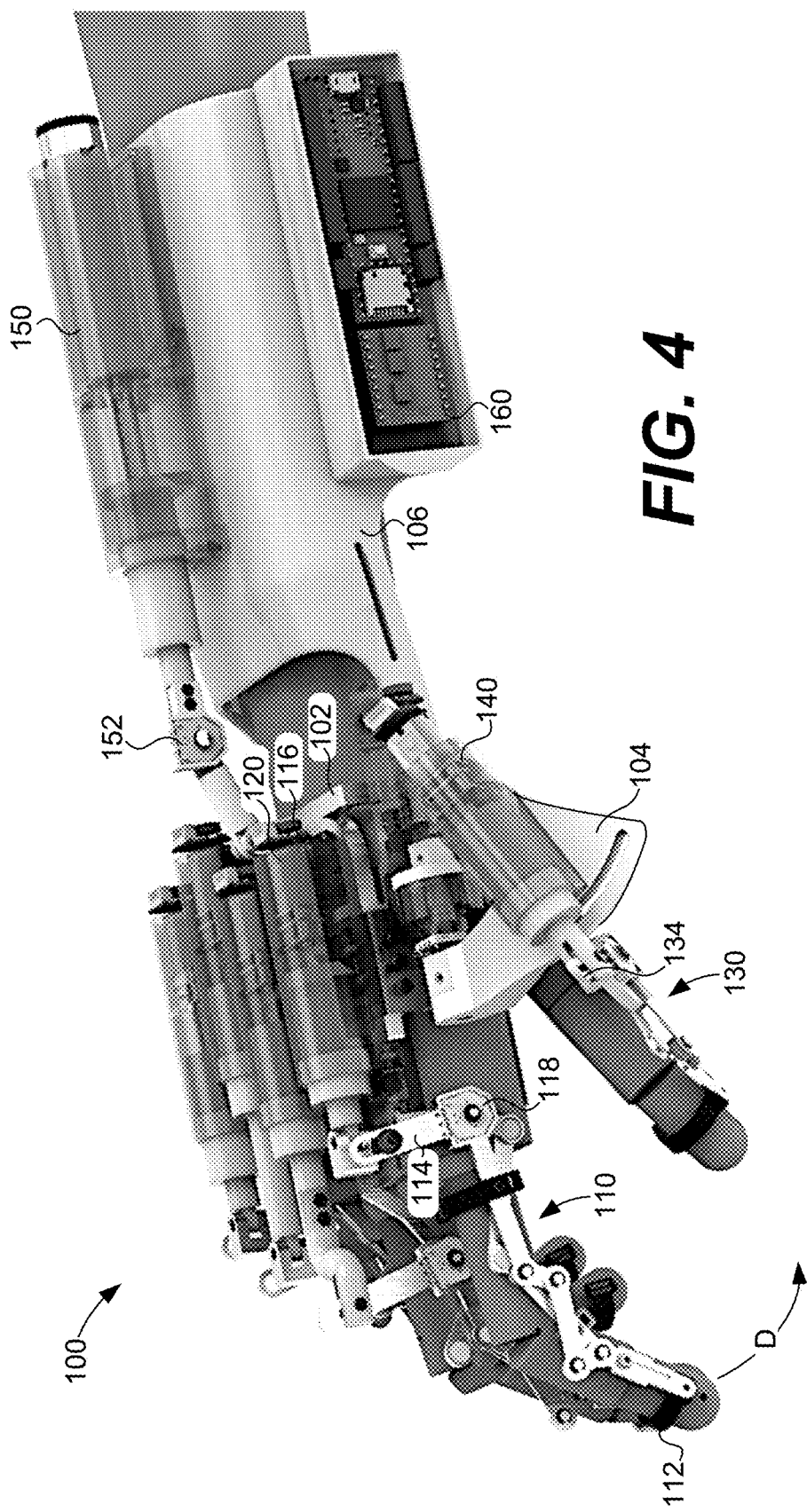
FIG. 4 illustrates another example exoskeleton glove system according to various aspects of the embodiments of the present disclosure.

FIG. 4 illustrates another example assistive exoskeleton glove system 100 ("glove system 100") according to various aspects of the embodiments of the present disclosure. The glove system 100 is provided as a representative example. The glove system 100 is not necessarily drawn to scale in FIG. 4, nor does FIG. 4 provide an exhaustive illustration of all components of the glove system 100. Additionally, one or more of the components shown in FIG. 4 can be omitted in some cases, and variations on the glove system 100 are described in further detail below.

Among other components, the glove system 100 includes a dorsum brace platform 102, a thumb brace platform 104, and a forearm brace platform 106. These platforms can be formed from one or more suitable materials, including leather, wood, plastic, metal, combinations thereof, or other materials. The dorsum brace platform 102 can be secured to the hand using a glove, one or more straps that fit or wrap around the palm, or other means. The dorsum brace platform 102 provides a relatively stable platform for other components of the glove system 100 as described below. The forearm brace platform 106 can be secured to the forearm using one or more straps that fit or wrap around the forearm, or other means. The forearm brace platform 106 provides a relatively stable platform for other components of the glove system 100 as described below.

The glove system 100 includes a number of finger braces, one of which is identified as finger brace 110 in FIG. 4. The glove system 100 also includes a thumb brace 130. The glove system 100 can include any number of finger braces. As shown in FIG. 4, the glove system 100 includes the finger brace 110 for the index finger, along with additional finger braces for the middle, ring, and pinky fingers, although one or more of the finger braces, and/or the thumb brace 130, can be omitted in some examples. The finger brace 110 can be secured to the index finger using a number of finger harnesses, including the finger harness 112, and the thumb brace 130 can be secured to the thumb using similar harnesses. The finger harness 112 can be embodied as any suitable type of strap or similar means that wraps around and secures the index finger to the finger brace 110. The mechanical design of the finger brace 110 is based on the kinematic model of the finger flexion brace 30 shown in FIGS. 3A and 3B, but optimized for size. Similarly, the mechanical design of the thumb brace 130 is based on the kinematic model of the thumb flexion brace 40 shown in FIG. 2, but optimized for size. Additional aspects of the finger brace 110 are described below with reference to FIGS. 5A and 5B.

The finger brace 110 includes an actuation lever 114, and the glove system 100 also includes an actuator 120 mounted and secured to the dorsum brace platform 102. An output shaft of the actuator 120 is mechanically coupled to the actuation lever 114. The actuator 120 is configured to articulate the finger brace 110 over a predetermined range of motion, which can be tailored for certain purposes, such as for grasping objects of a certain size or with a certain force. The glove system 100 also includes additional actuators to articulate the braces of the other fingers, as shown in FIG. 4. The output shaft of the actuator 120 extends linearly, in one example, to push or pull on the actuation lever 114. With that linear motion, the actuator 120 can articulate and curl the finger brace 110 in the direction D. The mechanics and actuation of the finger brace 110 is described in further detail below with reference to FIGS. 5A and 5B, and the actuator 120 is described in further detail below with reference to FIGS. 6A and 6B.

The thumb brace 130 also includes an actuation lever 134, and the glove system 100 also includes a thumb actuator 140 mounted and secured to the thumb brace platform 104. An output shaft of the thumb actuator 140 is mechanically coupled to the actuation lever 134. The thumb actuator 140 is configured to articulate the thumb brace 130 over a predetermined range of motion. The thumb actuator 140 extends linearly, in one example, to push or pull on the actuation lever 134. With that linear motion, the thumb actuator 140 can articulate and curl the thumb brace 130. Additionally, although it is obscured from view in FIG. 4, the glove system 100 includes a thumb flexion platform to control movement of the thumb brace platform 104. The range of motion of the thumb brace platform 104 for thumb flexion motion is described in further detail below with reference to FIG. 7.

The glove system 100 also includes a wrist actuator 150 mounted to the forearm brace platform 106. An output shaft of the wrist actuator 150 is mechanically coupled to the dorsum brace platform 102, to bend the wrist. The wrist actuator 150 can be designed to provide more force than the actuators 120 and 140, but the wrist actuator 150 can be of the same general design as the actuators 120 and 140. In other cases, the actuators 120, 140, and 150 can all be of the same or different designs.

The glove system 100 also includes a control system 160 and one or more batteries to power the control system 160, actuators, and other electrical systems of the glove system 100. Thus, the glove system 100 can be self-contained and operate without the need for an interface with other computing systems. As described in further detail below, the control system 160 can be embodied in hardware, software, or a combination of hardware and software.

The control system 160 can be embodied as an embedded control system (or part of such a control system) for the glove system 100. In that sense, the control system 160 can include one or more analog-to-digital converters, digital-to-analog converters, processor devices, memory devices, microcontrollers, accelerometers, motor drivers, and communications interfaces, among other control circuitry components, implemented using a combination of hardware and software, for example. The control system 160 can also include a local interface with data, address, and control lines for data communications with the feedback control system of the glove system 100, which includes a number of sensors, encoders, and other devices as described herein. In some cases, the control system 160 can also include a wired or wireless communication interface for communications external to the glove system 100. The control system 160 can also include one or more display interfaces, input/output interfaces, and other user interfaces and devices. For control of the actuators and other electromechanical systems of the glove system 100, the control system 160 can implement one or more proportional-integral (PI), proportional-derivative (PD), or proportional-integral-derivative (PID) controllers for such systems.

In one aspect, the control system 160 is configured to receive and process signals and other information from a feedback system. The feedback system can include a number of motion, position, acceleration, orientation, force, haptic, and other sensors and devices in the glove system 100. For example, the glove system 100 can include devices similar to the force sensors 50 and haptic feedback device 52 described above with reference to FIG. 2, among others. Such sensors and devices can be incorporated into the finger harness 112, for example, or other suitable locations on the glove system 100 to provide feedback to the control system 160 and the user of the glove system 100. This feedback can be used in several applications, such as providing haptic feedback for virtual reality applications, acting as a stimulus to prompt the user to perform certain tasks for rehabilitation, or as feedback for tele-navigation.

The glove system 100 can also include a number of encoders, including the encoders 116 and 118, among others, and the control system 160 can receive feedback signals from the encoders. Among various examples, the encoders 116 and 118 can be embodied as devices that convert motion or position information into an electrical signal for interpretation by the control system 160. The encoders 116 and 118 can provide a feedback signal that indicates relative or absolute angular position, speed, direction of motion or rotation, or other information.

In one example, the encoders 116 and 118 can be rotary position encoders for the finger brace 110, and other finger braces of the glove system 100 can include similar encoders. The encoder 116 can be referred to as a target encoder, and the encoder 118 can be referred to as an offset encoder. As described in further detail below, the control system 160 can detect a relative difference in the position or motion information provided between the encoders 116 and 118. This difference can be attributed in part to the elastic nature of the actuator 120, for example, when a user of the glove system 100 attempts to impart forces on the finger brace 110. The control system 160 can interpret the difference as feedback to help control the actuator 120, among other actuators or haptic feedback systems of the glove system 100.

In one example, the control system 160 can interpret the difference in the position information between the encoders 116 and 118, in real time, as a type of applied force feedback from a user of the glove system 100. The control system 160 can also calculate one or more metrics related to the forces applied on the finger brace 100 by the user, based on the applied force feedback, predetermined elastic constant(s) of elastic element(s) in the actuator 120, among others, and other factors. As examples, the control system 160 can calculate a magnitude and/or direction of the forces applied on the finger brace 100 by the user based on the applied force feedback. The control system 160 can also direct the actuator 120 for an autonomous grasp adjustment of the finger brace 110 based on a magnitude and/or direction of the forces applied on the finger brace 100. In this way, the glove system 100 can act as assistive and/or rehabilitation tool for users.

Overall, the control system 160 is configured to direct the overall operation of the glove system 100, by providing power and control signals to the actuators 120 and 140, among others, and receiving feedback signals from the encoders 116 and 118, among other sensors. As an example, the control system 160 can direct the actuator 120 to move the actuation lever 114 a certain distance, to articulate the finger brace 110 over a predetermined range of motion. The control system 160 can also monitor position or motion information provided from the encoders 116 and 118 while directing the actuator 120. Additional operations of the control system 160 are described below. The control system 160 can also include a memory to record and playback motions using the glove system 100. For example, the control system 160 can record the motions of a user's hand based on feedback collected by the glove system 100. The recorded motions can be analyzed by the control system 160 and/or other systems, as necessary. Additionally, the control system 160 can playback motions to the user's hand by articulating the actuator 120, among other actuators of the glove system 100, to direct the user's hand through a range of motions for assistive, rehabilitative, or other purposes. The control system 160 can also incorporate, through software control, a number of artificial intelligence and/or learning algorithms. The predetermined playback of motions can also be adjusted or augmented, in real time, based on the applied force feedback from a user of the glove system 100, as captured by the feedback system.

The control system 160 can also incorporate a voice user interface, using speech recognition to control the operation of the glove system 100. The control system 160 can be configured to recognize a number of voice commands, in various languages, such as "open," "close," "grasp," "release," and other commands. In other examples, a user can teach the control system 160 to recognize certain commands for one or more controls. The voice commands can be relied upon to operate individual digits (e.g., individual finger/thumb braces), perform grasping, pinching, or other motions, and perform certain tasks. In this sense, the glove system 100 can be embodied as a voice command device.

Figure 5A:
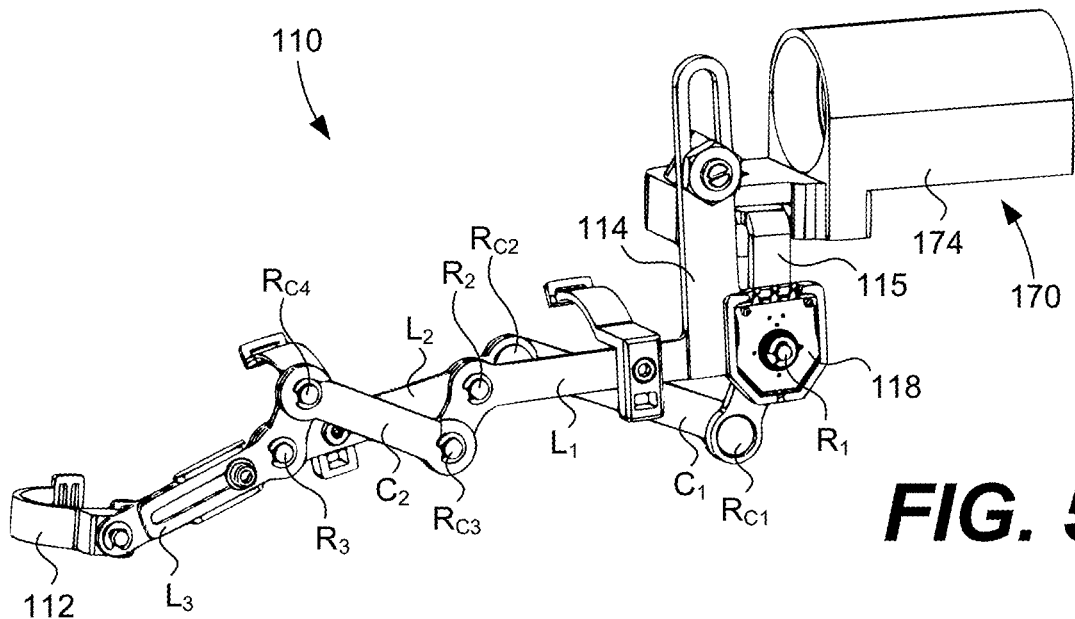
FIG. 5A illustrates a right-side view of an example finger brace of the exoskeleton glove system shown in FIG. 4 according to various aspects of the embodiments of the present disclosure.
Figure 5B:
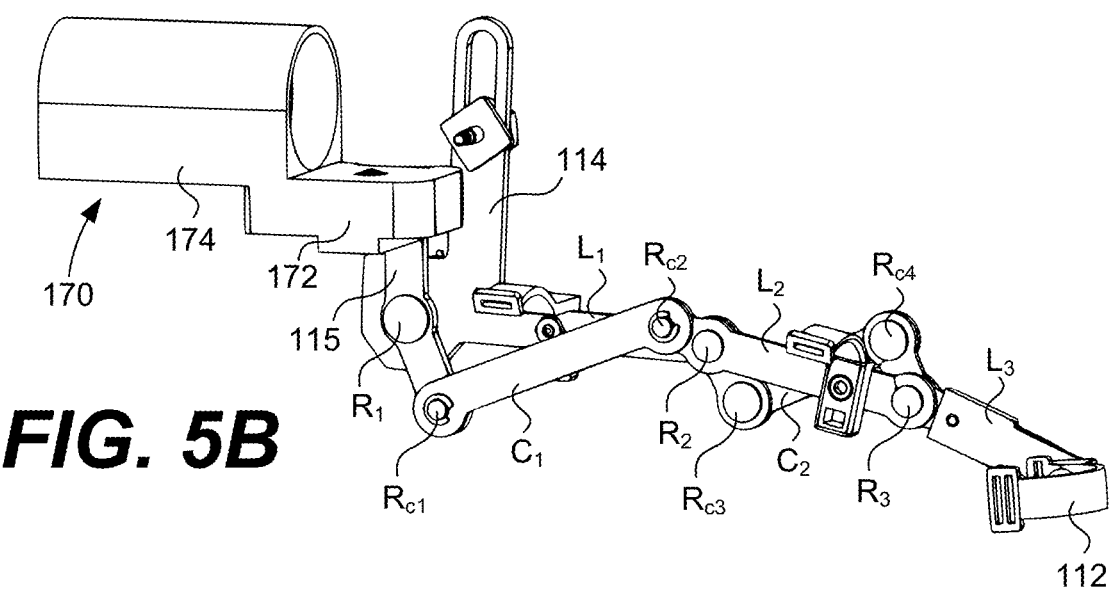
FIG. 5B illustrates a left-side view of the example finger brace shown in FIG. 5A according to various aspects of the embodiments of the present disclosure.

FIG. 5A illustrates a right-side view of the finger brace 110 of the glove system 100 shown in FIG. 4, and FIG. 5B illustrates a left-side view of the finger brace 110. As shown in FIGS. 5A and 5B, the finger brace 110 includes links $L_1$, $L_2$, and $L_3$, which correspond to the proximal, middle, and distal phalanges of the finger, respectively. The finger brace 110 also includes constraint links $C_1$ and $C_2$. The links $L_1$, $L_2$, and $L_3$ are connected to each other through three revolute joints, $R_1$, $R_2$, and, $R_3$. Specifically, links $L_1$ and $L_{i+1}$ are connected through revolute joint $R_{i+1}$. The constraint links $C_1$ and $C_2$ are used to produce the coupling relationship between the $L_i$ links. The constraint link $C_1$ connects the link $L_2$ to a fixed base frame (ground) by revolute joints $Rc_1$ and $Rc_2$. The constraint link $C_2$ connects links $L_1$ and $L_3$ through revolute joints $Rc_3$ and $Rc_4$. In the mechanical arrangement of the finger brace 110, link $L_1$ is connected to the ground at joint $R_1$, link $L_1$ is connected to link $L_2$ at joint $R_2$, and link $L_2$ is connected to link $L_3$ at joint $R_3$. Additionally, constraint link $C_1$ connects to the ground at constraint joint $Rc_1$ and to link $L_2$ at constraint joint $Rc_2$, and constraint link $C_2$ connects to link $L_1$ at constraint joint $Rc_3$ and to link $L_3$ at constraint joint $Rc_4$.

The mechanical and kinematic design of the finger brace 110 shown in FIGS. 5A and 5B is similar to that of the finger flexion brace 30 shown in FIGS. 3A and 3B, but optimized for size, weight, and function among other factors. The flexion and extension motions of the finger brace 110 can be achieved when a rotary motion is applied about the joint $R_1$, by pushing and pulling on the actuation lever 114. For example, the actuator 120 can be positioned in the actuator mount 174, or another suitable mount, and the output shaft of the actuator 120 can be mechanically coupled to the actuation lever 114 (see FIG. 4). The linear motion from the actuator 120 causes link $L_1$ to rotate about the joint $R_1$. As the link $L_1$ bends, the constraint links $C_1$ and $C_2$ translate the motion along to links $L_2$ and $L_3$. This collectively provides the coupling motion that reflects the natural flexion and extension of a human finger.

To design and optimize the finger brace 110, the lengths of the links, lengths of the constraint links, and positions of the revolute joints were determined based on the general dimensions of a human hand and the joint angles desired to be achieved. A kinematic model was relied upon for this purpose. The kinematic model for the finger brace 110 accounted for the following design parameters: $l_i$—length of link $L_i$, $c_i$—length of constraint link $C_i$, $\theta_i$—joint angle of link $L_i$, $d_i$—the radial distance of constraint joint $Rc_i$, expressed in local coordinates, and $\varphi_i$—the angle made by constraint joint $Rc_i$ in respect to the vertical Y axis. For the design described herein, suitable dimensions for the lengths of the links, lengths of the constraint links, and positions of the revolute joints were selected based on typical dimensions of a human hand, but other dimensions can be used in various embodiments.

The finger brace 110 is designed as a single DoF system. Particularly, the finger brace 110 is designed to articulate with a curling or grasping motion based on a single, linear motion provided by the actuator 120. One key characteristic of the finger brace 110 is its relatively thin profile. Flexion braces of a similar design can be positioned between one or more of the index finger and the middle finger, the middle finger and the ring finger, the ring finger and the pinky finger, and outside the pinky finger of the hand. Thus, the finger brace 110 of the glove system 100 can be extended for use with other digits other than the index finger and thumb, as outlined in the examples below.

For absolute and/or relative position sensing, the encoder 118 (FIG. 5A) can be placed on the $R_1$ joint of the finger brace 110, among other suitable joints. A signal from the encoder 118 can be captured by the control system 160, and correspond to the angular position of the $L_1$ link. The remaining joint angles of the PIP and DIP joints of the finger can be calculated by the control system 160 using the kinematic models of the finger brace 110. Using the kinematic model, the position of the link $L_3$ corresponding to the distal phalange of the index finger can also be calculated.

FIGS. 5A and 5B also illustrate a brace mount 170, and the brace mount 170 includes a pivot seat 172 and an actuator mount 174. A seat platform 115 of the finger brace 110 can be mechanically seated into the pivot seat 172, and the actuator 120 can be secured into the actuator mount 174. Further, the brace mount 170 can be secured to the dorsum brace platform 102 (FIG. 4). As described in further detail below with reference to FIG. 9, the glove system 100 includes an abduction/adduction mechanism for the finger brace 110, among others in the glove system 100. Particularly, the seat platform 115 is mechanically seated into the pivot seat 172 with a pivot, such that the abduction mechanism provides a rotational degree of freedom for the finger brace 110. Further, abduction springs provide a spring bias between the brace mount 170 and the seat platform 115.

Figure 6A:
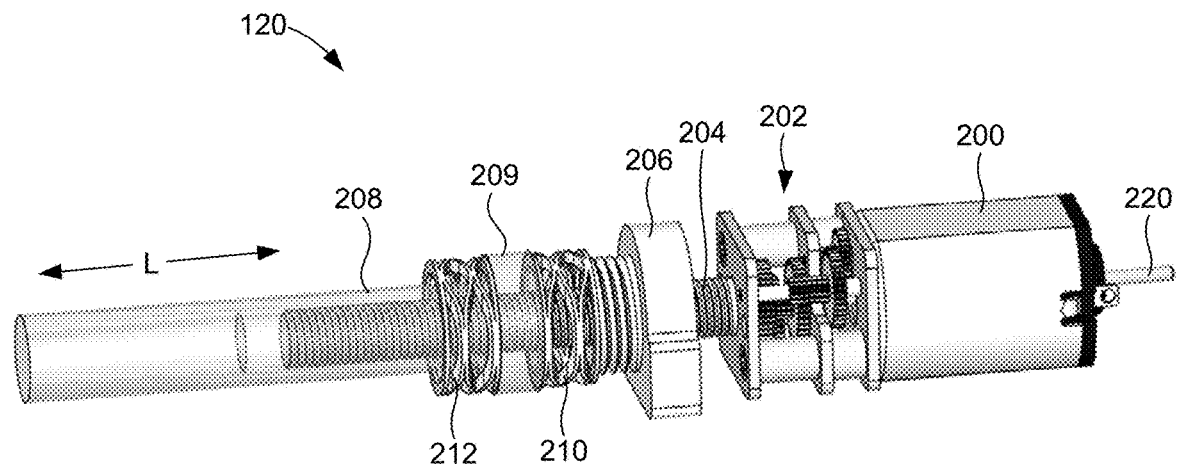
FIG. 6A illustrates an example series elastic actuator according to various aspects of the embodiments of the present disclosure.

Before turning to FIG. 6A, it is noted that the mechanical arrangement of the thumb brace 130 (FIG. 4) is similar to the finger brace 110 shown in FIGS. 5A and 5B, but the thumb brace 130 includes only links $L_1$ and $L_2$, which are connected by revolute joint $R_2$. The coupling action for the thumb brace 130 is achieved by a constraint link $C_1$, which connects link $L_2$ to the base frame through revolute joints $Rc_1$ and $Rc_2$.

FIG. 6A illustrates an example of the actuator 120 shown in FIG. 4 according to various aspects of the embodiments of the present disclosure. As shown, the actuator 120 is embodied as a linear series elastic actuator. The actuator 120 in FIG. 6A is illustrated as a representative example of one type of actuator that can be used in the glove system 100. The actuator 120 can be relied upon to move or operate the finger brace 110 of the glove system 100 for the index finger, and a number of similar actuators can be relied upon in the glove system 100 to operate finger braces for the middle, ring, and pinky fingers of the hand. Additionally, an actuator similar to the actuator 120 can be relied upon in the glove system 100 to operate the thumb brace 130. In other embodiments, the actuator 120 can be embodied as a hydraulic, pneumatic, piezoelectric, electromechanical, or other type of linear actuator.

Figure 7:
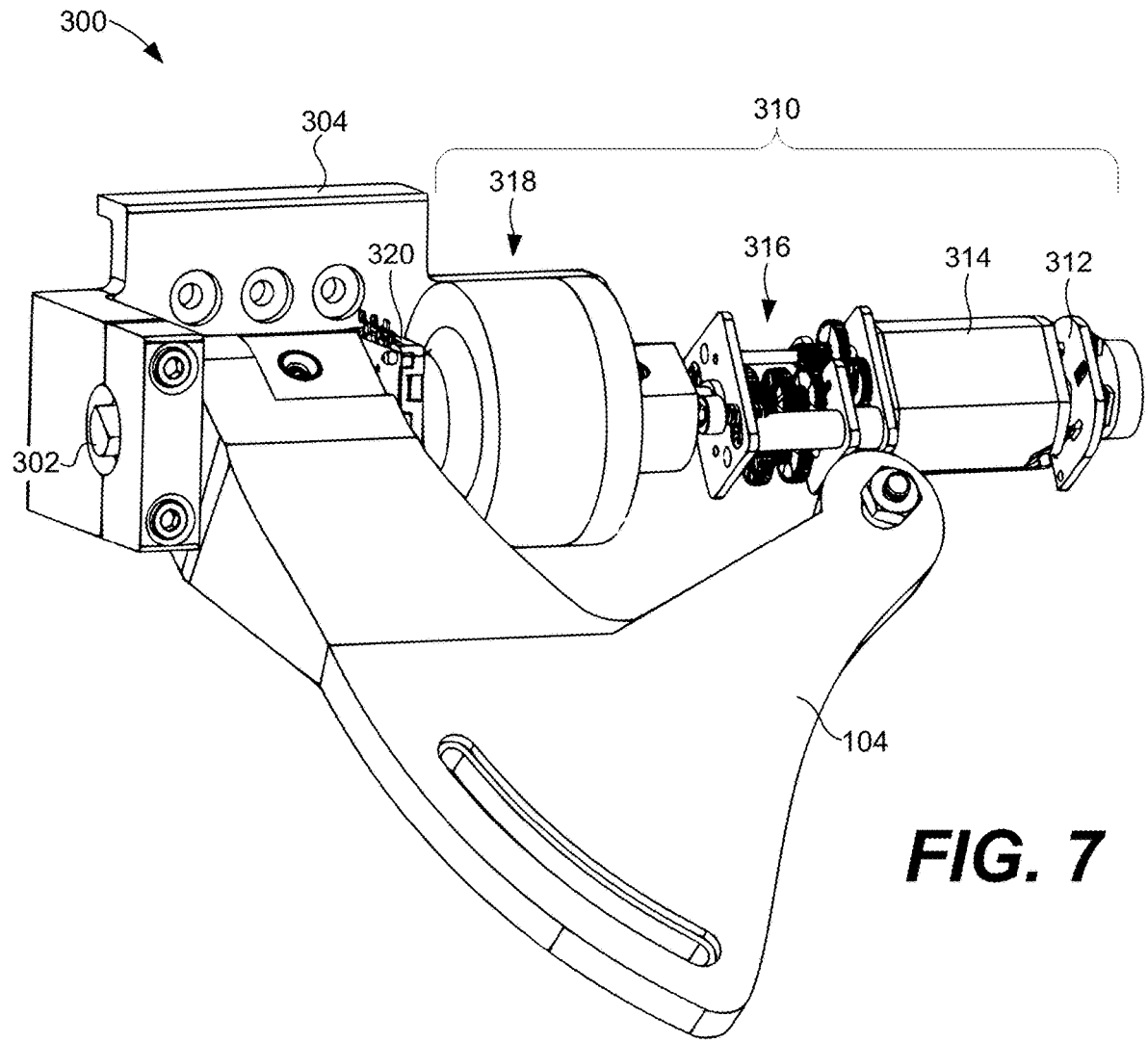
FIG. 7 illustrates an example thumb flexion platform according to various aspects of the embodiments of the present disclosure.

The casing or cover around the actuator 120 is omitted from view in FIG. 6A, so that the internal components of the actuator 120 can be illustrated. Among other components, the actuator 120 comprises a motor 200, a gearbox 202, a lead screw 204, a lead carriage 206, an output shaft 208, a first spring 210, and a second spring 212. Although not illustrated in FIG. 6A, and encoder can be installed over the rear output shaft 220. An example of such an encoder is illustrated in FIG. 7 and described below.

As examples, the motor 200 can be embodied as a brushed or brushless DC motor, such as a permanent magnet, stepper, series, shunt, or compound motor, although other types of motors can be relied upon. When the motor 200 is energized with power from the control system 160, an output shaft of the motor 200 can rotate, clockwise or counter-clockwise. The motor 200 can also include (or be coupled to) position, speed, force, torque, and other sensors, as described in further detail below, and the control system 160 can receive position, speed, and other data from the sensors to control the operation of the motor 200.

The motor 200 can be operated to turn an output shaft, and the output shaft of the motor 200 is mechanically coupled to the gearbox 202. An output shaft of the gearbox 202 is mechanically coupled to the lead screw 204. The gearbox 202 can be embodied as any arrangement of one or more gears between the motor 200 and the lead screw 204. The gearbox 202 can have a gear ratio that is suitable for translating sufficient force from the motor 200 for actuating the finger brace 110. The lead screw 204 can be selected to have a thread pitch, thread angle, and number of starts/threads for the speeds required to actuate the finger brace 110. The lead carriage 206 includes an inner thread that is mated to the thread pitch and thread angle of the lead screw 204. Thus, when the motor 200 is turned on, the lead screw 204 can be rotated in either clockwise or counter-clockwise directions. In turn, the lead carriage 206 moves forward or backward, linearly in the direction L, along the distance of the lead screw 204. As one example, the motor 200 and the gearbox 202 can be embodied as a Pololu® micrometal gearmotor with a 250:1 gear reduction and an output speed of 130 RPM. In this configuration, one design of the glove system 100 can travel a full 20 mm stroke for closing the finger brace 110 in approximately 0.659 seconds using a lead screw 204 with a 20 mm/rev lead.

Figure 6B:
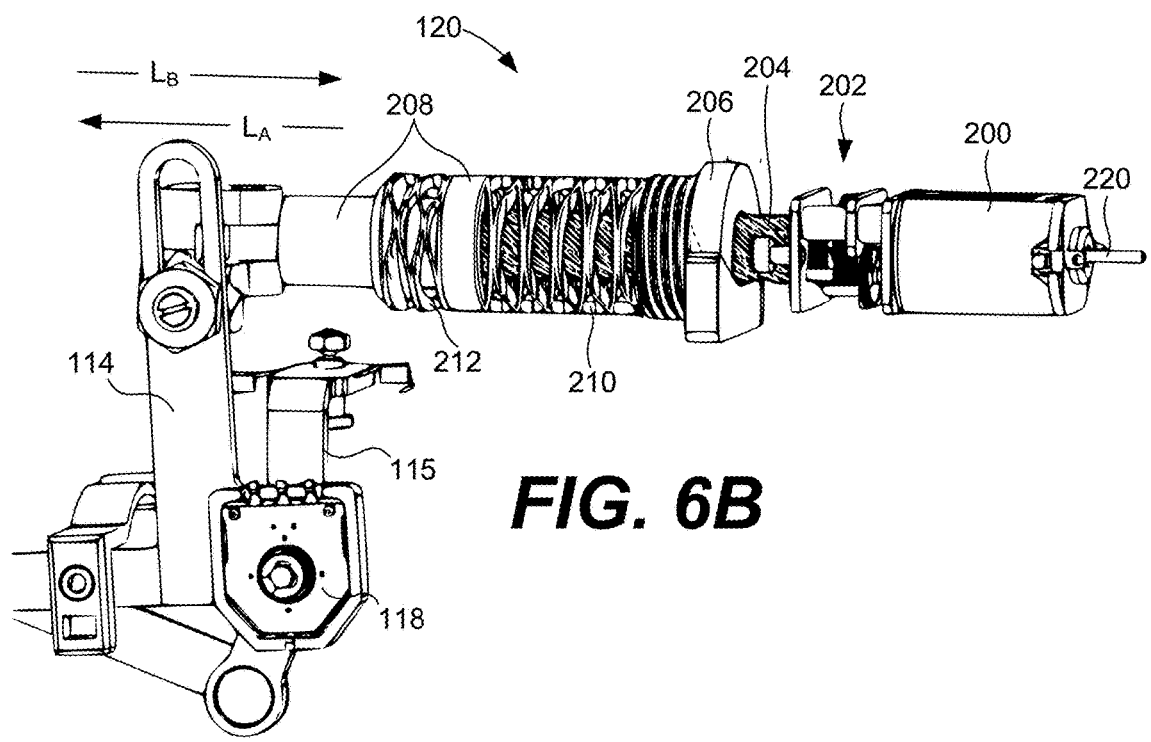
FIG. 6B illustrates the series elastic actuator shown in FIG. 6A mechanically coupled with the finger brace shown in FIG. 5A according to the embodiments of the present disclosure.

In one embodiment, the first spring 210 can be embodied as a type of wave or disc spring. The second spring 212 can also be embodied as a type of wave or disc spring. The first spring 210 and the second spring 212 are illustrated as representative examples in FIG. 6A. The number of turns or waves (e.g., the size) of the first spring 210 and the second spring 212 can be the same as shown in FIG. 6A, or the sizes of the springs can vary as compared to each other as shown in FIG. 6B. The size of the first spring 210 and the second spring 212 can also vary as compared to that shown in FIG. 6A. The first spring 210 and the second spring 212 can be formed from any suitable material, including plastic, metal, and other materials. The spring constant of the first spring 210 and the second spring 212 can be selected for the glove system 100 based on a number of factors, including the torque provided by the motor 200, the gear ratio of the gearbox 202, the thread pitch and thread angle of the lead screw 204, the strength of the hand, and other factors. The spring constant of the first spring 210 and the second spring 212 can be accounted for in the models processed by the control system 160, for accurate motions using the glove system 100.

The lead screw 204 extends through the first spring 210. In one example, the first spring 210 can be mechanically attached at one side to the lead carriage 206 and mechanically attached at another side to a head 209 of the output shaft 208. In this way, the first spring 210 can be both compressed and stretched within the actuator 120. The output shaft 208 extends through the second spring 212. The second spring 212 can also be mechanically attached at one side to a casing or other point of the actuator 120 and mechanically attached at another side to the head 209 of the output shaft 208. Thus, the second spring 212 can also be compressed and stretched within the actuator 120. In other examples, the first spring 210 and the second spring 212 are arranged in the actuator 120, with the head 209 of the output shaft 208 between the first spring 210 and the second spring 212, but it is not necessary that either or both of the springs 210 and 212 are mechanically attached to other components of the actuator 120.

In operation, the first spring 210 and the second spring 212 offer elasticity in the actuator 120, and this elasticity can be relied upon to provide certain features in the glove system 100. Trends in the development of exoskeleton gloves have relied upon soft actuators, despite their size and power requirements. On the other hand, the actuator 120 can provide compliant assistance while remaining compact and lightweight. Additionally, for the control of robotic exoskeletons, electromyography (EMG) sensors are often used to determine the intent of the user. However, the signal noise from EMG sensors is too large for direct determination of the desired operation, and prolonged placement of these sensors can be uncomfortable. Thus, according to one aspect of the embodiments, a dynamic feedback system can be realized using the actuator 120, by measuring the intended motions of a user through the compression of the first spring 210 and/or the second spring 212.

Feedback can also be provided to the control system 160, to account for energy stored in the first spring 210 and/or the second spring 212. In addition, the control system 160 is configured to account for a non-linear damping forces, to ensure that the glove system 100 does not exceed the physical range of the finger while ensuring stability during motion. In this regard, the glove system 100 can act as a positive admittance controller by increasing the displacement of the finger as determined by the physical spring displacement. Further, the control system 160 can execute prediction algorithms to analyze and predict intended motions of the user based on feedback, and assist the user with more specific grasping actions.

The integration of the actuator 120 with the finger brace 110 is shown in FIG. 6B. The brace mount 170 is omitted from view in FIG. 6B, so that the internal components of the actuator 120 can be seen. As shown, linear motion from the actuator 120 is transmitted to the slotted aperture of the actuation lever 114. The kinematic chain in the finger brace 110 causes synchronized curling motion along the MCP, PIP, and DIP joints of the index finger based on the linear motion from the actuator 120 as described herein. Particularly, for linear motion in the direction $L_A$, the kinematic chain in the finger brace 110 results in a curling motion, and for linear motion in the direction $L_B$, the kinematic chain in the finger brace 110 results in a uncurling motion. At the same time, an index finger secured along the finger brace 110 can impart forces upon the finger brace 110, and these forces can be translated back to the actuation lever 114 and the actuator 120. Thus, forces applied to the finger brace 110 can be translated into the actuator 120 and absorbed by one or both of the first spring 210 and the second spring 212.

In one example, the encoder 118 can be embodied as a rotary potentiometer, and the position of the finger can be encoded in a signal provided to the control system 160 by the rotary potentiometer located at the MCP joint of the finger. To determine the compression of the first spring 210 and/or the second spring 212 in the actuator 120, the control system 160 can calculate a difference between an expected location of the lead carriage 206 as compared to a measured location of the output shaft 208. The control system 160 can identify an expected location of the lead carriage 206 based on a signal provided by an encoder installed at the rear output shaft 220, as compared to a measured location of the output shaft 208.

The control system 160 can also calculate or measure a location of the output shaft 208 based on the feedback information provided from the encoder 118, along with data related to a mechanical model of the finger brace 110 and relative placement of the actuator 120 in the glove system 100, which is considered to be fixed, among other information. The difference between the expected location of the lead carriage 206 as compared to a measured location of the output shaft 208 is a metric of compression and/or extension in one or both of the first spring 210 and the second spring 212. The difference can be an indicator of forces translated from the finger to the actuator 120 and relied upon as a feedback input to the control system 160. In other words, the measurement of finger force feedback is possible by measuring spring compression in the actuator 120. In one embodiment, the control system 160 can rely upon this feedback to identify the intended motions of a user of the glove system 100. In other embodiments, the control system 160 can rely upon this feedback to identify the strength or force of the user.

To assist the motion of the user, the control system 160 can be configured to assume as though more energy was input into the actuator 120 than actually was. Furthermore, the control system 160 can be able to quickly stop motion if an antagonistic motion is performed, while also stopping in cases when the user may not have sufficient strength or control to stop the motion. Example optimizations of the control system 160 for these and other purposes are described in the publication titled "A Series Elastic Actuator Design and Control in a Linkage Based Hand Exoskeleton," proceedings of the ASME 2019 Dynamic Systems and Control Conference, Volume 3, Paper No. DSCC2019-8996, V003T17A003, published Nov. 26, 2019, the entire contents of which is hereby incorporated herein by reference.

FIG. 7 illustrates an example thumb flexion platform 300 according to various aspects of the embodiments of the present disclosure. As shown, the thumb flexion platform 300 includes the thumb brace platform 104, which is mechanically coupled to the thumb mount 304 at the pivot point 302. As shown in FIG. 4, the thumb mount 304 can be mounted on the dorsum brace platform 102. Further, the thumb actuator 140 and thumb brace 130 can be mounted on the thumb brace platform 104 as shown in FIG. 4. To pivot the thumb brace platform 104 about the pivot point 302, the thumb flexion platform 300 includes a rotational actuator 310.

The rotational actuator 310 includes an encoder 312, a motor 314, a gearbox 316, and a rotary elastic actuator 318. In one example, the motor 314 and the gearbox 316 can be similar to the motor 200 and the gearbox 202, as described in FIG. 6A, although different types of motors and gearboxes can be used. The encoder 312 can be secured to a rear output shaft of the motor 314, to provide a feedback signal to the control system 160. An output of the gearbox 316 is mechanically coupled to the rotary series elastic actuator 318. The rotary series elastic actuator 318 includes a rotary series elastic component, which is described in further detail below with reference to FIGS. 8A and 8B. An output shaft of the rotary elastic actuator 318 is mechanically coupled to the thumb brace platform 104, to pivot the thumb brace platform 104 about the pivot point 302.

The control system 160 can measure the angular orientation of the thumb brace platform 104 based on a feedback signal provided from the encoder 320. The difference between the angular orientation of the thumb brace platform 104, as measured by the encoder 320, as compared to the position information provided from the encoder 312, is a metric of elastic energy stored in the rotary series elastic actuator 318. The difference can be an indicator of forces translated from the thumb to the thumb brace platform 104 and relied upon as a feedback input to the control system 160. In other words, the measurement of thumb flexion force feedback is possible by measuring elastic energy stored in the rotary series elastic actuator 318. In one embodiment, the control system 160 can rely upon this feedback to identify the intended motions of a user of the glove system 100. In other embodiments, the control system 160 can rely upon this feedback to identify the strength or force of the user.

Figure 8A:
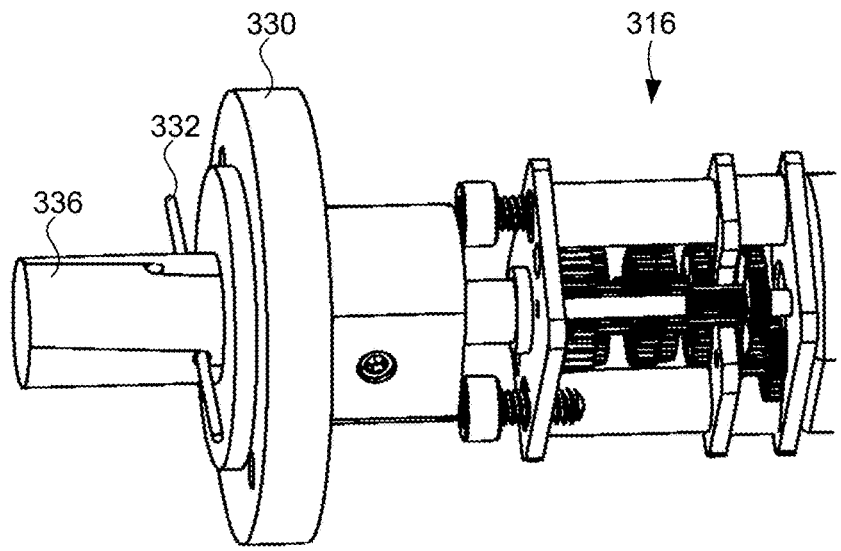
FIG. 8A illustrates components of an example rotary series elastic actuator in the glove system shown in FIG. 4 according to various aspects of the embodiments of the present disclosure.
Figure 8B:
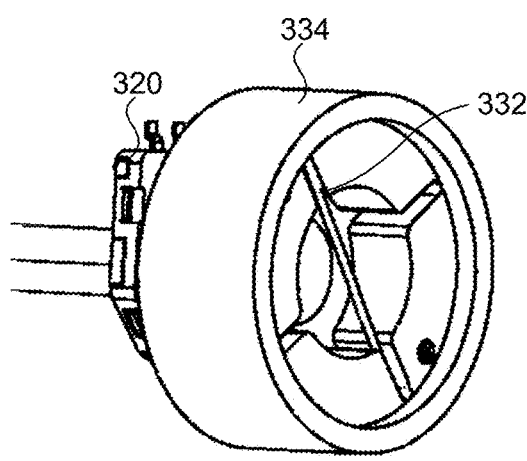
FIG. 8B illustrates example elastic components of the rotary series elastic actuator shown in FIG. 8A according to various aspects of the embodiments of the present disclosure.
Figure 8C:
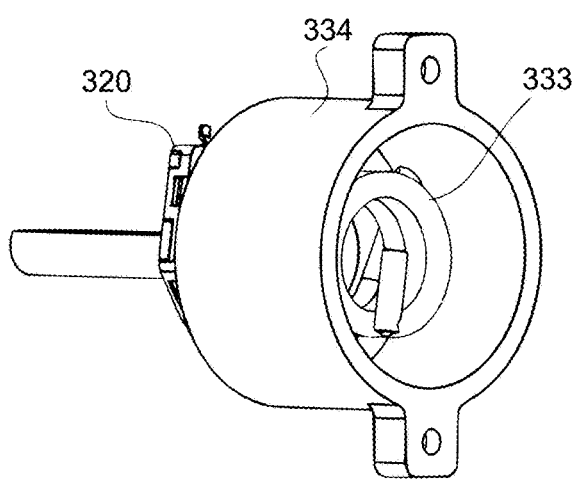
FIG. 8C illustrates other example elastic components of the rotary series elastic actuator shown in FIG. 8A according to various aspects of the embodiments of the present disclosure.

FIGS. 8A, 8B, and 8C illustrate example components of the rotary series elastic actuator 318 shown in FIG. 7. Referring between FIGS. 8A, 8B and 8C, the rotary series elastic actuator 318 includes an inner housing 330 of the rotary series elastic actuator 318, an outer housing 334 of the rotary series elastic actuator 318, and an elastic element fitted between the inner housing 330 and the outer housing 334. In various examples, the elastic element can be a translation beam 332 (FIG. 8B), a torsion spring 333 (FIG. 8C), or another suitable elastic element fitted between the inner housing 330 and the outer housing 334. The translation beam 332 or the torsion spring 333 is mechanically interposed between the inner housing 330 and the outer housing 334. In one example, as shown in FIG. 8A, the translation beam 332 extends through an aperture in a cylindrical plug 336 of the inner housing of the rotary series elastic actuator 318. As also shown in FIG. 8B, the translation beam 332 fits into a longitudinal channel in the outer housing 334 of the rotary series elastic actuator 318. In another example, the torsion spring 333 can be mechanically coupled between the inner housing 330 and the outer housing 334.

When the inner housing 330 of the rotary series elastic actuator 318 is twisted with respect to the outer housing 334 of the rotary series elastic actuator 318, rotational energy is translated between them through the translation beam 332 or the torsion spring 333. The translation beam 332 can be embodied as a relatively thin cylindrical (or square or other profile) beam of plastic, metal, or other material, having suitable shear strength to translate forces between the inner housing 330 and the outer housing 334. The translation beam 332 can also be flexible enough to absorb rotational forces between the inner housing 330 and the outer housing 334. The translation beam 332 can also be implemented as the torsion or rotational spring 333, or any other suitable elastic element in any shape or form fitted between the inner housing 330 and the outer housing 334 of the rotary series elastic actuator 334.

Referring again to FIG. 7, the control system 160 can measure the angular orientation of the thumb brace platform 104 based on a feedback signal provided from the encoder 320. The difference between the angular orientation of the thumb brace platform 104, as measured by the encoder 320, as compared to the position information provided from the encoder 312, is a metric of elastic energy stored by the translation beam 332 or the torsion spring 333 present inside the rotary series elastic actuator 318. The difference can be an indicator of forces translated from the thumb to the thumb brace platform 104 and relied upon as a feedback input to the control system 160.

Figure 9A:
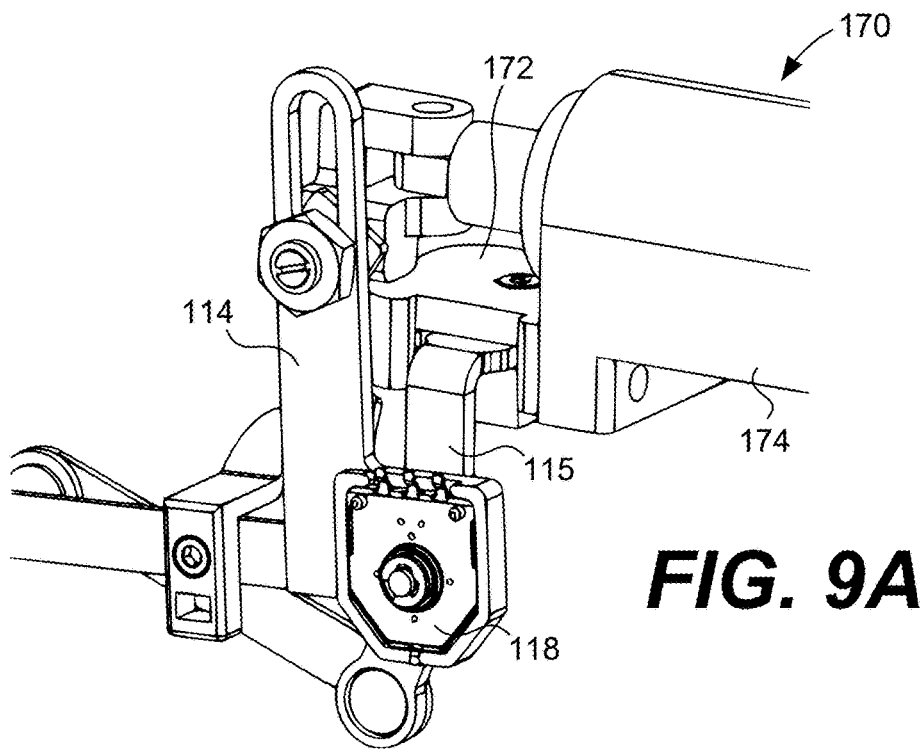
FIG. 9A illustrates components of an abduction/adduction mechanism in the glove system shown in FIG. 4 according to various aspects of the embodiments of the present disclosure.
Figure 9B:
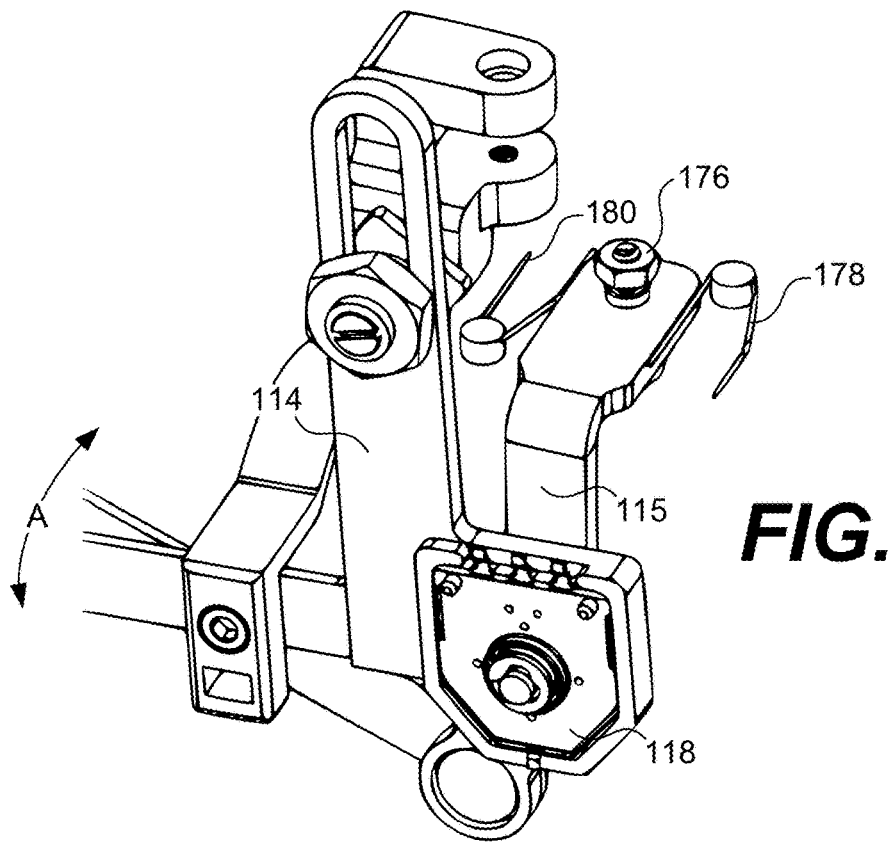
FIG. 9B illustrates other components of abduction/adduction mechanism shown in FIG. 9A according to various aspects of the embodiments of the present disclosure.

FIGS. 9A and 9B illustrate components of an abduction mechanism in the glove system 100 according to various aspects of the embodiments of the present disclosure. FIG. 9A illustrates the brace mount 170 in which the actuator 120 is secured. The brace mount 170 includes a pivot seat 172 for the seat platform 115 of the finger brace 110. The brace mount 170 is omitted from view in FIG. 9B, so that the seat platform 115 and internal components of the pivot seat 172 can be seen.

Referring between FIGS. 9A and 9B, the seat platform 115 of the finger brace 110 can be mechanically seated into the pivot seat 172. Particularly, the seat platform 115 is mechanically seated into the pivot seat 172 at a pivot 176, such that the abduction mechanism provides a rotational degree of freedom for the finger brace 110 in the direction A. Further, abduction springs 178 and 180 provide a spring bias between the brace mount 170 and the seat platform 115, to bias the finger brace 110 into a straight orientation.

The control system 160 can be embodied in hardware, software, or a combination of hardware and software. In one example, the control system 160 includes at least one processor or processing device and at least one memory or memory device, both of which are electrically and communicatively coupled to a local interface. The local interface can be embodied as a data bus with an accompanying address/control bus or other addressing, control, and/or command lines, for data communications and addressing between the processor, the memory, and the feedback control system of the glove system 100.

In various embodiments, the memory device stores data and other software or executable-code components executable by the processor. The data can be related to the operation of the glove system 100 and the user of the glove system 100. Where any component discussed herein is implemented in the form of software, any one of a number of programming languages can be employed such as, for example, C, C++, C#, Objective C, JAVA®, JAVASCRIPT®, Perl, PHP, VISUAL BASIC®, PYTHON®, RUBY, FLASH®, or other programming languages. Thus, the memory device can store software for execution by the processor. In this respect, the terms "executable" or "for execution" refer to software forms that can ultimately be run or executed by the processor, whether in source, object, machine, or other form. Examples of executable programs include, for example, a compiled program that can be translated into a machine code format and loaded into a random access portion of the memory and executed by the processor, source code that can be expressed in an object code format and loaded into a random access portion of the memory and executed by the processor, or source code that can be interpreted by another executable program to generate instructions in a random access portion of the memory and executed by the processor, etc.

In various embodiments, the memory can include both volatile and nonvolatile memory and data storage components. Volatile components are those that do not retain data values upon loss of power. Nonvolatile components are those that retain data upon a loss of power. Thus, the memory can include, a random access memory (RAM), read-only memory (ROM), magnetic or other hard disk drive, solid-state, semiconductor, universal serial bus (USB) flash drive, memory card, optical disc (e.g., compact disc (CD) or digital versatile disc (DVD)), floppy disk, magnetic tape, or any combination thereof. In addition, the RAM can include, for example, a static random access memory (SRAM), dynamic random access memory (DRAM), or magnetic random access memory (MRAM), and/or other similar memory device. The ROM can include, for example, a programmable read-only memory (PROM), erasable programmable read-only memory (EPROM), electrically erasable programmable read-only memory (EEPROM), or other similar memory device. An executable program can be stored in any portion or component of the memory.

The processor can be embodied as one or more microprocessors, one or more discrete logic circuits having logic gates for implementing various logic functions, application specific integrated circuits (ASICs) having appropriate logic gates, and/or programmable logic devices (e.g., field-programmable gate array (FPGAs), and complex programmable logic devices (CPLDs)).

If embodied in software, the control system 160 can include a module or group of code that includes program instructions to implement the specified logical function(s). The program instructions can be embodied in the form of source code that includes human-readable statements written in a programming language or machine code that includes machine instructions recognizable by a suitable execution system, such as a processor in a computer system or other system. Thus, the processor can be directed by execution of the program instructions to perform certain processes. In the context of the present disclosure, a non-transitory computer-readable medium can be any tangible medium that can contain, store, or maintain any logic, application, software, or executable-code component described herein for use by or in connection with an instruction execution system.

Also, one or more of the components described herein that include software or program instructions can be embodied in a non-transitory computer-readable medium for use by or in connection with an instruction execution system, such as the control system 160. The computer-readable medium can contain, store, and/or maintain the software or program instructions for execution by or in connection with the instruction execution system. The computer-readable medium can include a physical media, such as, magnetic, optical, semiconductor, and/or other suitable media or drives. Further, any logic or component described herein can be implemented and structured in a variety of ways. For example, one or more components described can be implemented as modules or components of a single application. Further, one or more components described herein can be executed in one computing device or by using multiple computing devices.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

Therefore, the following is claimed:

1. An assistive system for a hand of an individual, comprising:
    a brace mount;
    a finger brace comprising a seat platform mechanically coupled to the brace mount, the finger brace further comprising a plurality of brace links, a plurality of constraint links, and an actuation lever;
    an actuator mechanically coupled to the actuation lever and configured to articulate the finger brace over a predetermined range of motion;
    a feedback system configured to monitor motion of the finger brace, the feedback system comprising a target encoder mounted to the actuator and an offset encoder mounted to the finger brace; and
    a control system configured to:
        receive applied force feedback from the feedback system;
        calculate a metric of applied force on the finger brace based on the applied force feedback and an elastic constant of an elastic element in the actuator; and
        direct the actuator for an autonomous grasp adjustment based on the metric of applied force.

2. The assistive system of claim 1, wherein the actuator comprises a linear series elastic actuator.

3. The assistive system of claim 1, wherein the actuator comprises a motor, a gearbox, a lead screw, a lead carriage, and an output shaft.

4. The assistive system of claim 3, wherein the actuator further comprises at least one spring between the lead carriage and the output shaft.

5. The assistive system of claim 1, further comprising an abduction/adduction mechanism configured to provide a rotational degree of freedom for the finger brace.

6. The assistive system of claim 5, wherein:
    the abduction/adduction mechanism comprises a pivot post and an abduction/adduction spring in the brace mount;
    the seat platform comprises a pivot aperture;
    the seat platform is positioned in the brace mount with the pivot post extending through the pivot aperture; and
    the abduction/adduction spring provides a spring bias between the brace mount and the seat platform.

7. The assistive system of claim 1, wherein:
    the finger brace comprises one finger brace among a plurality of finger braces of the assistive system; and
    the actuator comprises one actuator among a plurality of actuators for the plurality of finger braces of the assistive system.

8. The assistive system of claim 1, further comprising:
    a thumb brace mount;
    a thumb brace mechanically coupled to the thumb brace mount, the thumb brace comprising a plurality of thumb brace links, a plurality of thumb constraint links, and a thumb actuation lever;
    a thumb actuator mechanically coupled to the thumb actuation lever and configured to articulate the thumb brace; and
    a thumb flexion actuator mechanically coupled to the thumb brace mount and configured to articulate the thumb brace mount over a range of thumb flexion motion.

9. The assistive system of claim 8, wherein:
    the thumb actuator further comprises a rotary series elastic actuator; and
    the rotary series elastic actuator comprises an inner rotational translator, an outer rotational translator, and an elastic element mechanically interposed between the inner rotational translator and the outer rotational translator.

10. The assistive system of claim 1, wherein:
    the applied force feedback comprises a relative difference in feedback signals provided from the target encoder and the offset encoder, as a measure of deflection in the elastic element in the actuator.

11. An assistive system for a hand of an individual, comprising:
    a finger brace comprising a plurality of brace links, a plurality of constraint links, and an actuation lever;
    a finger actuator mechanically coupled to the actuation lever and configured to articulate the finger brace over a predetermined range of motion;
    a thumb brace comprising a plurality of thumb brace links, a plurality of thumb constraint links, and a thumb actuation lever;
    a thumb actuator mechanically coupled to the thumb actuation lever and configured to articulate the thumb brace;
    a feedback system configured to monitor motion of the finger brace, the feedback system comprising a target encoder mounted to the finger actuator and an offset encoder mounted to the finger brace; and a control system configured to:
- receive applied force feedback from the feedback system;
- calculate a metric of applied force on the finger brace based on the applied force feedback and an elastic constant of an elastic element in the finger actuator; and
- direct the finger actuator for an autonomous grasp adjustment based on the metric of applied force.

12. The assistive system of claim 11, wherein the finger actuator comprises a lead carriage, an output shaft, and a spring between the lead carriage and the output shaft.

13. The assistive system of claim 11, further comprising an abduction/adduction mechanism configured to provide a rotational degree of freedom for at least one of the finger brace or the thumb brace.

14. The assistive system of claim 11, wherein the finger brace comprises one finger brace among a plurality of finger braces of the assistive system.

15. The assistive system of claim 11, wherein:
- the thumb actuator further comprises a rotary series elastic actuator; and
- the rotary series elastic actuator comprises an inner rotational translator, an outer rotational translator, and an elastic element mechanically interposed between the inner rotational translator and the outer rotational translator.

16. The assistive system of claim 13, wherein:
- the applied force feedback comprises a relative difference in feedback signals provided from the target encoder and the offset encoder, as a measure of deflection in the elastic element in the finger actuator.

* * * * *